United States Patent
Yang

(10) Patent No.: US 11,292,630 B2
(45) Date of Patent: Apr. 5, 2022

(54) SIMPLY PACKAGED STYLUS-TYPE SYRINGE NEEDLE AND USE METHOD THEREFOR

(71) Applicant: JB MEDICAL, INC., Wujiang (CN)

(72) Inventor: Jibin Yang, Sparta, NJ (US)

(73) Assignee: JB MEDICAL, INC., Wujiang (CN)

( * ) Notice: Subject to any disclaimer, the term of this patent is extended or adjusted under 35 U.S.C. 154(b) by 131 days.

(21) Appl. No.: 15/539,133

(22) PCT Filed: Dec. 23, 2015

(86) PCT No.: PCT/CN2015/000922
§ 371 (c)(1),
(2) Date: Jun. 22, 2017

(87) PCT Pub. No.: WO2016/101336
PCT Pub. Date: Jun. 30, 2016

(65) Prior Publication Data
US 2017/0349315 A1    Dec. 7, 2017

(30) Foreign Application Priority Data

Dec. 24, 2014 (CN) .......................... 201410808498.4

(51) Int. Cl.
*B65B 69/00* (2006.01)
*A61M 5/00* (2006.01)
*A61M 5/31* (2006.01)

(52) U.S. Cl.
CPC ............. *B65B 69/00* (2013.01); *A61M 5/002* (2013.01); *A61M 5/31* (2013.01)

(58) Field of Classification Search
CPC ......... B65B 69/00; A61M 5/002; A61M 5/31; A61M 5/3202; A61M 5/3205
See application file for complete search history.

(56) References Cited

U.S. PATENT DOCUMENTS

| 5,944,700 A | 8/1999 | Nguyen et al. |
| 2012/0037655 A1* | 2/2012 | DiBiasi ............... A61M 5/3202 221/1 |
| 2014/0165505 A1* | 6/2014 | Banik ..................... B65B 43/00 53/456 |

FOREIGN PATENT DOCUMENTS

| CN | 101806752 A | 8/2010 |
| CN | 101832947 A | 9/2010 |

(Continued)

OTHER PUBLICATIONS

International Patent Application No. PCT/CN2015/091957 filed Oct. 15, 2015 in the name of JB Medical, Inc., 26 pages.
(Continued)

*Primary Examiner* — Anthony D Stashick
*Assistant Examiner* — L Kmet
(74) *Attorney, Agent, or Firm* — Birch, Stewart, Kolasch & Birch, LLP

(57) ABSTRACT

The present invention disclosed a simply packaged pen needle and methods of use, comprising of at least one needle body and at least one packaging body used to package said needle body, where said needle body is comprised of a needle hub, a cannula, and an inner protective cap connected consecutively, said packaging body comprises of a packaging cup and the sealing paper, said packaging cup comprises of at least one chamber coupled with said needle body, said needle hub comprises of at least one axial protrusion on its outer circumference, the inner wall of said chamber comprises of at least one groove coupled with the axial protrusion, the upper edge of said chamber is a flat surface, said sealing paper connects with the flat surface. As a result, this simply packaged pen needle and methods of use will simplify the entire manufacturing and sealing processes, significantly enhance the reliability of sterile sealing, greatly (Continued)

reduce product cost, especially suitable for mass production, thus is of great economic value.

18 Claims, 4 Drawing Sheets

(56) References Cited

FOREIGN PATENT DOCUMENTS

| | | |
|---|---|---|
| CN | 102303017 A | 1/2012 |
| CN | 102448527 A | 5/2012 |
| CN | 103134811 A | 6/2013 |
| CN | 104483321 A | 4/2015 |
| CN | 104528082 A | 4/2015 |
| EP | 2420267 A | 2/2012 |
| JP | 2009092474 A | 4/2009 |
| JP | 2014034461 A | 2/2014 |
| WO | 2013122941 A | 8/2013 |
| WO | 2016066017 A | 5/2016 |

OTHER PUBLICATIONS

International Search Report issued in International Patent Application No. PCT/CN2015/091957 dated Jan. 11, 2016, 5 pages.
Written Opinion of the International Searching Authority issued in International Patent Application No. PCT/CN2015/091957 dated Jan. 11, 2016, 5 pages.
International Patent Application No. PCT/CN2015/000922 filed Dec. 23, 2015 in the name of JB Medical, Inc.
International Search Report issued in International Patent Application No. PCT/CN2015/000922 dated Apr. 1, 2016.
Chinese Patent Application No. 201410808498.4, filed on Dec. 24, 2014 in the name of JB Medical, Inc.
Written Opinion of the International Searching Authority issued in International Patent Application No. PCT/PCT/CN2015/000922 dated Apr. 2016.
Chinese Notification to Register and English translation for Application No. 201410808498.4, dated Aug. 2, 2016.
Chinese Office Action and English translation for Application No. 201410808498.4, dated Jan. 28, 2016.
Chinese Office Action and English translation for Application No. 201410808498.4, dated Jun. 24, 2016.
European Search Opinion for Application No. 15871415.4, dated Aug. 20, 2018.

* cited by examiner

SIMPLY PACKAGED STYLUS-TYPE SYRINGE NEEDLE AND USE METHOD THEREFOR

CROSS-REFERENCE TO RELATED APPLICATIONS

The present application is a National Stage of International Patent Application No. PCT/CN2015/000922, 23 Dec. 2015, which claims foreign priority benefits under 35 U.S.C 119 to Chinese Patent Application No. 201410808498.4 (CN) filed 24 Dec. 2014.

TECHNICAL FIELDS

The present invention relates to the field of sterile packaging of medical pen needles, especially relates to the simply packaged pen needle and methods of use.

BACKGROUND

The existing pen needle, as shown in FIG. 1 to FIG. 3, is sealed up using an outer protective cap 1 and medical sealing paper 2. To use, tear the sealing paper 2 at bonding point 3 off from outer protective cap 1 to expose sterile needle 5 (needle hub and cannula 7), screw onto the injection pen 4, pull off outer protective cap 1 and inner protective cap 6 to expose the needle cannula 7, after injection is completed, at least cover with the outer protective cap 1, unscrew the pen needle off the injection pen 4. This type of primary packaging structure, using outer protective cap 1 and a separate sealing paper 2, puts very stringent demand on the automatic production process, especially when stamping off the water-drop-shaped sealing paper 2, precision must be guaranteed to ensure the product information printed on its surface stay in the right position, it also requires highly accurate relative positions between sealing paper 2 and outer protective cap 1 in heat bonding process. Other disadvantages of the existing type of primary packaging includes that it requires an extra process for bonding sealing paper and outer protective cap 1 at bonding point 3, plus a bag or a box is required when packaging a plurality of pen needles together whose precision counting process is very complicated, clearly, the pen needle production is costly due to the high precision production process coupled with the complicated assembly process.

Invention

The present invention provides a simply packaged pen needle and methods of use, in which the conventional outer protective cap is not needed, merely put a needle body, comprising of a needle hub, a cannula and an inner protective cap, into a packaging cup, then seal up the packaging cup with sealing paper.

To solve the above technical problem, the present invention provides a simply packaged pen needle and methods of use, comprising at least one needle body and at least one packaging body used to package said needle body, wherein said needle body comprises of a needle hub, a cannula, and an inner protective cap connected consecutively, wherein said packaging body comprises of a packaging cup and sealing paper, wherein said packaging cup comprises of at least one chamber coupled with said needle body, wherein said needle hub comprises of at least one axial protrusion on its outer circumference, wherein the inner wall of said chamber comprises of at least one groove coupled with said axial protrusion;

In a preferred embodiment, the external diameter and width of said groove's upper portion is larger than the outer diameter and width of said axial protrusion.

In a preferred embodiment, the external diameter and width of said groove's lower portion is smaller than the outer diameter and width of said axial protrusion.

In a preferred embodiment, wherein said packaging cup comprises of at least 2 chambers, the surface between adjacent chambers has a dividing line to separate said adjacent chambers.

In a preferred embodiment, wherein a polygonal area is set at a corner of said packaging body on said flat surface, said packaging body and sealing paper are not bonded within the said polygonal area.

The present invention also provides methods of use for the simply packaged pen needle, said simply packaged pen needle can be any one type of pen needles as described in claims 1 to 5 and is comprised of the following steps:

(1) detach a packaging body containing a needle body from other packaging body or bodies along the dividing line,
(2) tear off the sealing paper starting from the polygonal area,
(3) hold onto the recessed area on packaging cup and screw said needle body onto injection pen, then pull out said packaging cup,
(4) take off the inner protective cap of said needle body, expose the cannula,
(5) put said packaging cup back onto said needle body after injection is completed,
(6) unscrew said needle body and packaging cup off the injection pen, place them back into said chamber of said packaging body.

The present invent possesses the following advantages:

(1) no need for the outer protective cap, which reduces the manufacturing and assembly cost,
(2) increased bonding area between the sealing paper and the packaging cup, which makes sealing process a lot easier, thus significantly increases the reliability of the sterile sealing, and will better ensure the sterile production and packaging of pen needles,
(3) comparing to the stamping of water-drop-shaped sealing paper, cutting of the sealing paper in the present invention is a lot easier, because it is a straight line cut along the dividing line on the packaging cup, and the sporadically connected dividing line on the packaging cup ensures that a plurality of packaged pen needles are connected and easily torn off by hand,
(4) a pack made of a plurality of packaging cups can be the packaging body in itself, no box is needed, which eliminates the complicated counting process for box packaging, thus reduces cost of the overall pen needle production and use,
(5) convenient online printing of partial or the entire user's manual and product information onto the surface of sealing paper eliminates the cost of packaging a separate user's manual,
(6) manner of use is basically unchanged, thus is easy to be accepted by users.

In sum, the entire production process has significantly reduced the product cost, and is especially suitable for mass production, thus is of great economic value.

DESCRIPTION OF DRAWINGS

Constituting a part of this application, the accompanying drawings are included to provide a further understanding of the invention, exemplary embodiments of the present invention and descriptions thereof are used to explain the present invention, and do not constitute improper limitation to the present invention. In the drawings.

A PREFERRED EMBODIMENT

Figure 1:
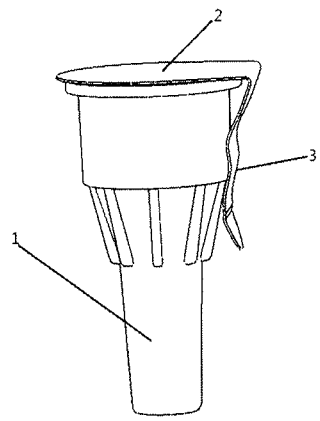
FIG. 1 is a structural diagram of the structure of an existing pen needle.
Figure 2:
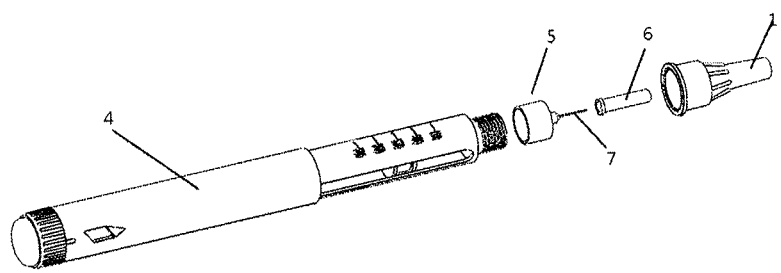
FIG. 2 is a structural diagram of how the existing pen needle is mounted to an injection pen.
Figure 3:
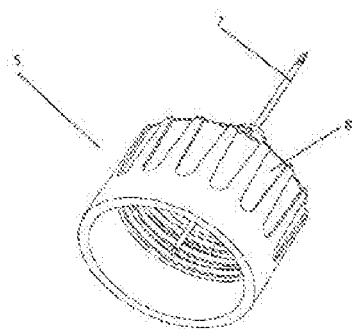
FIG. 3 is a structural diagram of an existing pen needle after the cannula is assembled to a needle hub.

The following is a preferred embodiment of the technical aspects of the present invention. Obviously, the embodiment is only exemplary of the technical aspects of the present invention, not in its entirety. All other embodiments, obtained by persons of skills in the field from or out of the subject invention without having to put in any creative effort, falls within the protective scope of the present invention.

Referring to FIG. 4A-FIG. 6, an embodiment of the present invention comprises of:

A simply packaged pen needle comprising of: at least one needle body 9 and at least one packaging body to package the needle body 9, the said needle body 9 comprises of a needle hub, a cannula 7 and an inner protective cap 6 connected consecutively, the said packaging body comprises of a packaging cup 10 and sealing paper 13, the said packaging cup 10 comprises of a plurality of chambers coupled with the said needle body 9, the said needle hub comprises of 4 axial protrusions 11 on its outer circumference, the inner wall of the said chamber comprises of 4 grooves 12 coupled with the 4 axial protrusions 11, the upper edge of said chamber has a flat surface, the said sealing paper 13 connects with the said flat surface, that is, the flat surface at the top of packaging cup 10 bonds with the sealing paper 13 to realize the sterile sealing of the pen needle. The external diameter $D_2$ of the upper portion of the grooves 12 is slightly larger than the outer diameter $D_1$ of the upper portion of the axial protrusions 11 to facilitate the plugging in of needle body 9, the external diameter of the said grooves 12 of packaging cups' 10 lower portion is slightly smaller than the outer diameter of the axial protrusions 11 to ensure needle body 9 is fixed inside packaging cup 10. In addition, the width $W_2$ of an upper portion of grooves 12 is slightly larger than a width $W_4$ of the upper portion of axial protrusions 11 and the width $W_1$ of a lower portion of grooves 12 is slightly smaller than the width $W_3$ of a lower portion of axial protrusions 11. The needle hub of existing pen needle comprises of a plurality of grooves 8 coupled with the outer protective cap 1, which makes the needle rotates together with the outer protective cap. Needle body 9 of the present invention does not need an outer protective cap, the outer circumference of the needle hub comprises of 4 axial protrusions 11, which can not only provide an increased rigidity to the needle hub, but also couple with the grooves 12 on the packaging cup 10, plus only a twist at the recessed area of packaging cup 10 is required when mounting the needle body 9 on to an injection pen, said recessed area is formed at the outer surface of two adjacent grooves 12.

Figure 4A:
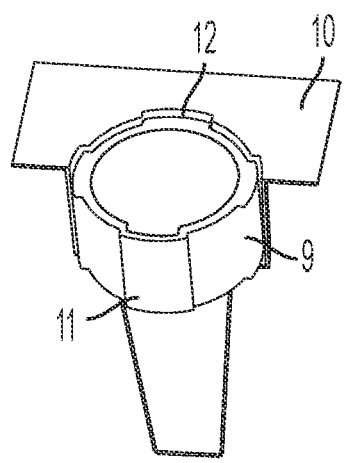
FIG. 4A is the present invention's simply packaged pen needle—partial view of a preferred embodiment of a pen needle body assembled in a packaging cup.
Figure 4B:
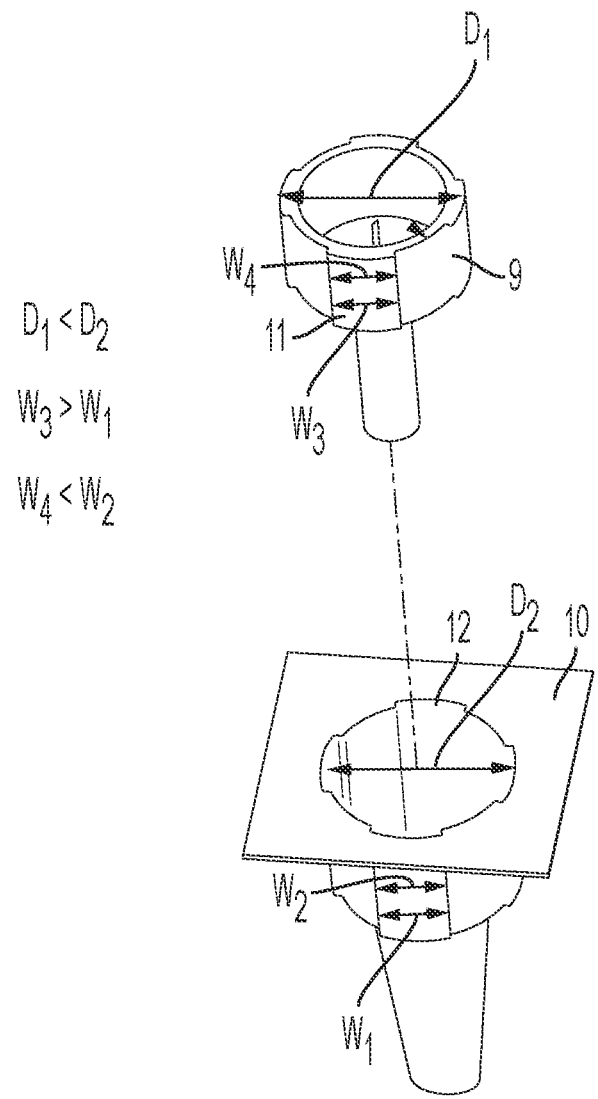
FIG. 4B is an exploded view of the pen needle body and partial view of the packaging cup.
Figure 5:
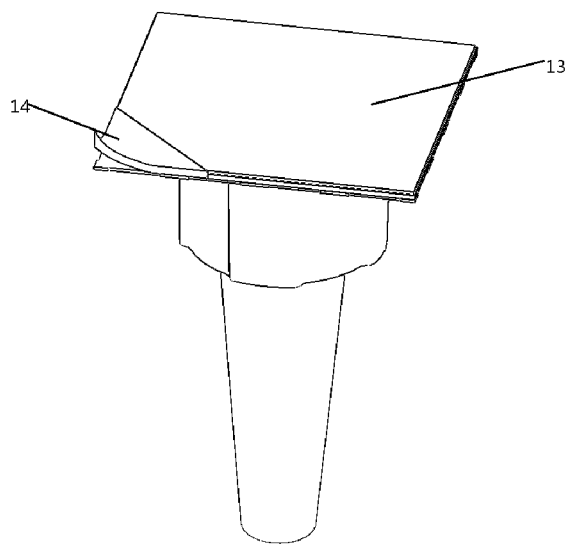
FIG. 5 is a structural diagram of a packaged pen needle in FIG. 4A sealed inside a packaging cup with sealing paper.
Figure 6:
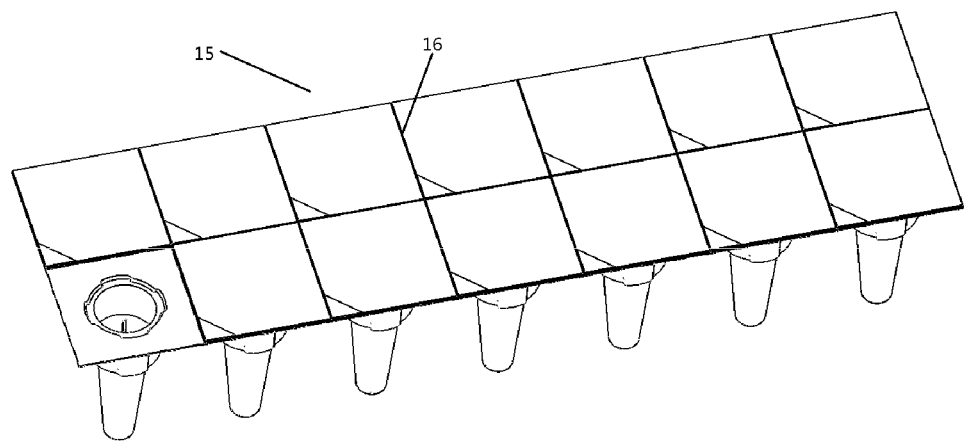
FIG. 6 is a structural diagram of a plurality of simply packaged pen needles packaged together.

As seen in FIG. 4, the cup 10 has a sidewall forming a chamber to receive the needle body. A flange extends outwardly from a top edge off the sidewall. The sidewall has grooves 12 which mate with the protrusions 11 on the needle hub of the needle body. The protrusions 11 extend an entire axial length of the needle hub. Therefore, the grooves extend an entire axial length of the sidewall. The upper end of each groove extends into the flange, creating an irregular shaped opening in the top surface of the flange. As seen in FIG. 6, the opening in the flange has a circular shape with radially outwardly extending notches having a shape corresponding to the grooves.

This type of packaging body does not need an outer protective cap, it reduces the overall manufacturing and assembling cost, makes cutting of the sealing paper 13 very easy as it is a straight line cut along the dividing line 16, the bonding area between sealing paper 13 and packaging cup 10 is greatly increased which makes the sealing process a lot easier, thus significantly increases the reliability of the sterile sealing, which will ensure the sterile production and packaging of the pen needle.

Furthermore, a polygonal area 14 is set at a corner of the packaging body on the flat surface where the flat surface of said packaging body and sealing paper 13 meet, said packaging body and sealing paper are not bonded within the said polygonal area 14. As long as the sealing properties are not affected, a polygonal area 14 is set at the corner along an edge where packaging cup 10 and sealing paper 13 meet, the simplest example of a polygonal area is a triangle where sealing paper 13 and packaging cup 10 are not bonded within this triangular area. The easiest way to make it unbounded is to make sure that there is no boding material within this triangular area, thus sealing paper 13 can be conveniently torn off within polygonal area 14 when pen needle is to be used.

In addition, said packaging cup 10 has 2 chambers, the surface between adjacent chambers has a dividing line 16 to separate the adjacent chambers, of course, as shown in FIG. 6, to make it easy for mass production, transportation and use, a plurality of needle body 9 can be connected together according to a certain shape which makes a pack 15. This embodiment shows a 2-row, 14-needle pack, which can be arranged into any shape. There is a dividing line 16 between the needle bodies 9. To use, one needle can be torn off along the diving line 16. To ensures an easy separation of packaging bodies, the dividing line 16 between the needle bodies 9 is comprised of 2 parts: (1) dividing line 16 on packaging cup 10 can be set when said packaging cups are formed so that packaging cups are connected but can be easily torn by hand, (2) dividing line 16 on sealing paper 13 can be cut-open, or connected sporadically but can be easily separated. Of course, partial or the entire user's manual and product information can be very conveniently printed on the surface of sealing paper 13 to provide easy access for users.

The methods of use of the said pen needle is comprised of the following steps:

(1) detach a packaging body of needle body 9 from other packaging bodies along dividing line 16, (2) tear off sealing paper 13 starting from polygonal area 14, (3) hold onto recessed area on packaging cup 10 and screw needle body 9 onto the injection pen, then pull out the packaging cup 10, (4) take off the inner protective cap 6 of needle body 9, expose the cannula, (5) put said packaging cup 10 back onto said needle body 9 after injection is completed,
(6) unscrew said needle body 9 and packaging cup 10 off the injection pen, place them back into said chamber of said packaging body.

Different from the existing technologies, the advantages of the simply packaged pen needle and methods of use are as follows:
(1) no need for the outer protective cap, which reduces the manufacturing and assembly cost,
(2) increased bonding area between the sealing paper and the packaging cup, which makes sealing process a lot easier, thus significantly increases the reliability of the sterile sealing, and will better ensure the sterile production and packaging of pen needles,
(3) comparing to the stamping of water-drop-shaped sealing paper, cutting of the sealing paper in the present invention is a lot easier, because it is a straight line cut along the dividing line on the packaging cup, and the sporadically connected dividing line on the packaging cup ensures that a plurality of packaged pen needles are connected and easily torn off by hand,
(4) a pack made of a plurality of packaging cups can be the packaging body in itself, no box is needed, which eliminates the complicated counting process for box packaging, thus reduces cost of the overall pen needle production and use,
(5) convenient online printing of partial or the entire user's manual and product information onto the surface of sealing paper eliminates the cost of packaging a separate user's manual,
(6) manner of use is basically unchanged, thus is easy to be accepted by users.

In sum, the entire production process of the present invention greatly reduces the product cost, is especially suitable for mass production, and is of great economic value.

The above is only a preferred embodiment of the present invention, not intend to restrict the protective scope of the invention. Any equivalent structural or procedural change made from or out of the description of this invention or direct or indirect use thereof in any related technical field fall within the protective scope of this patent.

The invention claimed is:

1. A simply packaged pen needle comprising:
at least one needle body; and
at least one packaging body used to package said needle body,
wherein said needle body comprises a needle hub, a cannula, and an inner protective cap connected consecutively,
wherein said packaging body comprises at least one packaging cup comprising a sidewall and a flange extending radially outwardly from the sidewall,
wherein said packaging cup comprises a chamber formed by the sidewall and coupled with said needle body,
wherein said needle hub comprises a plurality of protrusions on an outer surface and spaced from each other in a circumferential direction of the needle hub, each protrusion having a height and a width,
wherein an inner surface of said chamber comprises a plurality of grooves spaced from one another in a circumferential direction of the sidewall,
wherein each of the plurality of protrusions is coupled with one of the plurality of grooves when the needle hub is in the chamber, and
wherein a width of a lower portion of at least one of the plurality of grooves is smaller than a width of a lower portion of one of the plurality of protrusions when the needle hub is in the chamber.

2. A simply packaged pen needle according to claim 1, wherein a width of an upper portion of the at least one of the plurality of grooves is larger than a width of an upper portion of one of the plurality of protrusions.

3. A simply packaged pen needle according to claim 1, wherein said at least one packaging cup comprises at least two packaging cups, the flanges of the at least two packaging cups being connected to one another, and
wherein a dividing line extends between the flanges of the at least two packaging cups.

4. A simply packaged pen needle according to claim 3, further comprising sealing paper bonded to the flange,
wherein a polygonal area is set at a corner of the flange, and
wherein the flange and the sealing paper are not bonded within the said polygonal area.

5. A method of use of a simply packaged pen needle according to claim 1, the method comprising:
tearing off sealing paper attached to the at least one packaging body,
holding onto the packaging cup and screwing said needle body onto an injection pen, then removing said needle body out of said packaging cup,
taking off the inner protective cap of said needle body, exposing the cannula,
putting said packaging cup back onto said needle body after injection is completed, and
unscrewing said needle body and packaging cup off the injection pen, placing them back into said chamber of said packaging body.

6. The method of use of a simply packaged pen needle according to claim 5, wherein the needle body is screwed onto the injection pen by twisting only.

7. A simply packaged pen needle according to claim 1, wherein the plurality of protrusions is four protrusions.

8. A simply packaged pen needle according to claim 1, wherein the at least one of the plurality of protrusions comprises a first surface spaced radially outwardly from the outer circumference of the needle hub and a pair of side surfaces, each side surface extending between the outer surface of the needle hub and the first surface.

9. A simply packaged pen needle according to claim 1, wherein a top surface of each of the plurality of projections is coplanar with a top surface of the needle hub.

10. A simply packaged pen needle according to claim 1, wherein a number of protrusions equals a number of grooves.

11. A simply packaged pen needle according to claim 1, further comprising sealing paper,
wherein the flange has a flat surface connected with said sealing paper.

12. A simply packaged pen needle according to claim 1, wherein one of the plurality of grooves extends between each pair of the plurality of protrusions.

13. A simply packaged pen needle according to claim 1, wherein the needle hub further comprises a sidewall and a bottom wall attached to a first edge of the sidewall, the cannula extending from the bottom wall, and
wherein each of the plurality of projections extends an entire height of the sidewall of the needle hub.

14. A simply packaged pen needle according to claim 1, wherein the at least one chamber comprises an upper chamber and a lower chamber, and
wherein each of the plurality of grooves extends an entire height of the upper chamber.

15. A simply packaged pen needle according to claim 1, wherein each of the plurality of protrusions comprises a first surface spaced radially outwardly from the outer circumference of the needle hub and a pair of side surfaces, each side surface extending between the outer surface of the needle hub and the first surface, and wherein the side surfaces of the plurality of protrusions are spaced from one another in a circumferential direction of the needle hub over the entire height of each of the protrusions.

16. A simply packaged pen needle according to claim 1, wherein the plurality of protrusions are spaced from each other over an entire height of each of the protrusions.

17. A simply packaged pen needle according to claim 1, wherein a width of a lower portion of at least one of the plurality of grooves is smaller than a width of at least one of the plurality of protrusions.

18. A simply packaged pen needle according to claim 1, wherein an external diameter of an upper portion of at least one of the plurality of grooves is larger than an outer diameter of an upper portion of at least one of the plurality of protrusions, and wherein the at least one of the plurality of protrusions extends into the at least one of the plurality of grooves when the needle hub is in the packaging cup.

\* \* \* \* \*